United States Patent [19]

Narayanan et al.

[11] Patent Number: 4,819,640

[45] Date of Patent: Apr. 11, 1989

[54] MICROSURGERY ANASTOMOSIS TOOL

[75] Inventors: Krishna Narayanan; Marc D. Liang; Frank R. Walters, all of Pittsburgh, Pa.

[73] Assignee: The Montefiore Hospital Association of Western Pennsylvania, Pittsburgh, Pa.

[21] Appl. No.: 914,164

[22] Filed: Oct. 1, 1986

[51] Int. Cl.⁴ .............................................. A61B 17/04
[52] U.S. Cl. ................................................ 128/334 R
[58] Field of Search ........................... 128/334 R, 335; 223/104; 139/380, 381; 132/75.4; D28/57; 81/6

[56] References Cited

U.S. PATENT DOCUMENTS

| 251,183 | 12/1881 | Bullock | 81/6 |
| 2,613,562 | 10/1952 | Clark | 81/6 |

FOREIGN PATENT DOCUMENTS

| 1176130 | 10/1984 | Canada | 128/334 |
| 1239068 | 4/1967 | Fed. Rep. of Germany | 132/75.4 |
| 11727 | of 1907 | United Kingdom | 139/381 |

OTHER PUBLICATIONS

Artree, "A Hook for Placement of Bridle Sutures", David E. Eifrig, M.D., Arch. Ophthal., vol. 88, Oct. 1972.

Primary Examiner—Richard C. Pinkham
Assistant Examiner—Gary Jackson
Attorney, Agent, or Firm—Harry B. Keck

[57] ABSTRACT

A microsurgery tool for use in anastomosis of small vessels has a thin shaft with a pair of forwardly projecting tines defining a throat for receiving the pointed end of a suture needle. The microsurgery tool is inserted between confronting ends of vessels into engagement with the inner wall of one vessel for receiving a suture needle point passing through the outer wall of the vessel and thereafter is withdrawn from the space between the vessels to engage the outer surface of the other vessel where it receives the pointed end of the same suture needle passing through the inner wall of the other vessel.

2 Claims, 2 Drawing Sheets

MICROSURGERY ANASTOMOSIS TOOL

BACKGROUND OF THE INVENTION

1. Field of the Invention

This invention relates to a microsurgery tool to be used in anastomosis of small vessels, e.g., veins and arteries.

2. Description of the Prior Art

Microsurgery procedures require anastomosis of small vessels, e.g., veins and arteries, which may have a diameter of 0.4–1.5 millimeters. When open ends of such small vessels are to be joined (anastomosis) the recommended procedure is to provide 6 to 8 sutures for a vein-to-vein connection and 7 to 9 sutures for an artery-to-artery connection. Typical sutures are 0.3 to 0.4 millimeters wide. Because of the size of the vessels and sutures, these procedures are carried out with use of a microscope and are referred to as microsurgery techniques.

Overwhelmingly, such anatomosis procedures employ a clamping device which secures the cut ends of the vessel in alignment. See U.S. Pat. No. 4,553,542. A normal procedure employs microsurgery forceps which are inserted through the open end into one of the vessels and allowed to spring open whereby the vessel end region is dilated to facilitate puncture of that vessel with a suture needle. The forceps are withdrawn and inserted through the open end of the other vessel for dilation and the suture needle point punctures the dilated vessel surface. The suture needle is extracted from both vessels and the trailing suture is tied. This sequence is repeated numerous times for each vessel. The initial sutures are usually spaced diametrically apart on the vessels and can be applied without significant difficulty. Subsequent sutures however are quite difficult with the microsurgery forceps technique because of the small size of the vessels. Typically, anastomosis of a single vessel using the microsurgery forceps techinques may require about one hour of surgical time. The success of overall surgical procedures frequently depends upon the success of blood vessel anastomosis procedures. An alternative existing procedure employs a ring device which is mounted annularly from the anastomosis site as described in U.s. Pat. No. 4,474,181. This procedure dilates the ends of the vessels and maintains the anastomosis suture connection in a dilated condition by connecting each suture to the annular ring. Each suture is normally applied with the microsurgery forcepts techniques when a ring device is used.

STATEMENT OF THE PRESENT INVENTION

A microsurgery tool is provided which functions in cooperation with a suture needle in small vessel anastomosis. The microsurgery tool has a thin shaft with a pair of forwardly extending tines defining a throat. The microsurgery tool is inserted into one of the two vessels and interiorally supports the vessel wall. A surgical needle point is inserted through the outer wall of the vessel into the throat of the microsurgery tool and is directed by the tool through the vessel open end. Thereupon the microsurgery tool is withdrawn and placed on the other vessel outer wall and the suture needle point punctures the inner wall of the other vessel and appears in the throat of the microsurgery tool. Thereafter the microsurgery tool is withdrawn, the suture needle is extracted through both vessels and the trailing suture is tied. The procedure is repeated as many times as required to provide a satisfactory anastomosis.

DESCRIPTION OF THE PREFERRED EMBODIMENTS

Figure 6:
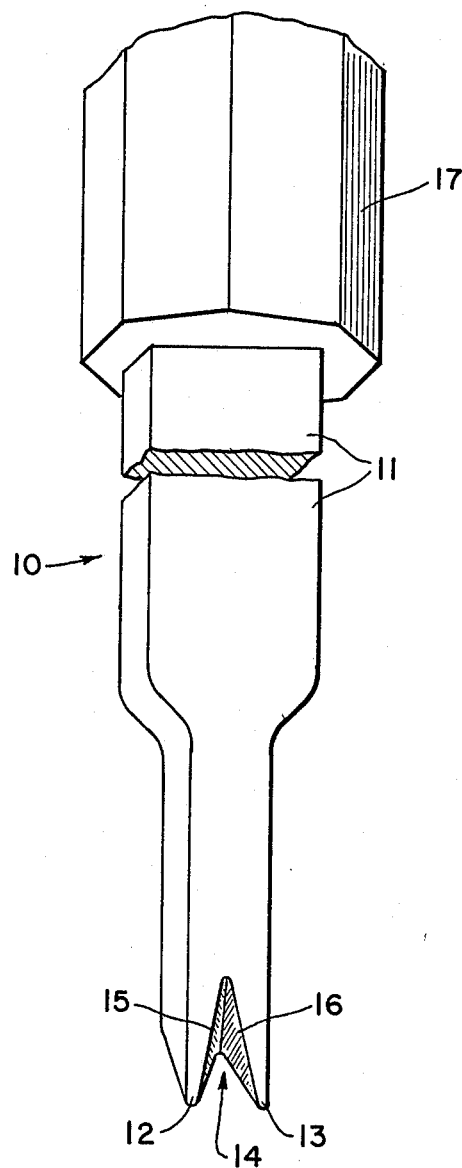
FIG. 6 is an enlarged view of an alternative embodiment of the invention.

The microsurgery tool of this invention can be illustrated in one embodiment in FIG. 6 which shows the microsurgery tool 10 having a thin shaft 11 and a pair of tines 12, 13 extending forwardly from the shaft defining a throat 14 therebetween. The confronting surfaces 15, 16 of the tines 12, 13 are sloping surfaces which intersect along a line which is angularly presented with respect to the central longitudinal axis of the shaft. The confronting surfaces 15, 16 thereby provide a scoop-like configuration to the throat 14. The microsurgery tool 10 is secured to holding means 17 illustrated schematically in FIG. 6. The main body portion of the microsurgery tool 11 is illustrated as a multi-flat surfaced rod in FIG. 6. In a preferred embodiment, the main body portion of the microsurgery tool 11 is a cylindrical rod or a tapered cylinder rod. The thin shaft preferably is from 1 to 4 millimeters in diameter and about 10 to 30 millimeters long. The tines 12, 13 project for about 1 to 3 millimeters, providing a throat opening about 1 to 2 millimeters deep.

Figure 7:
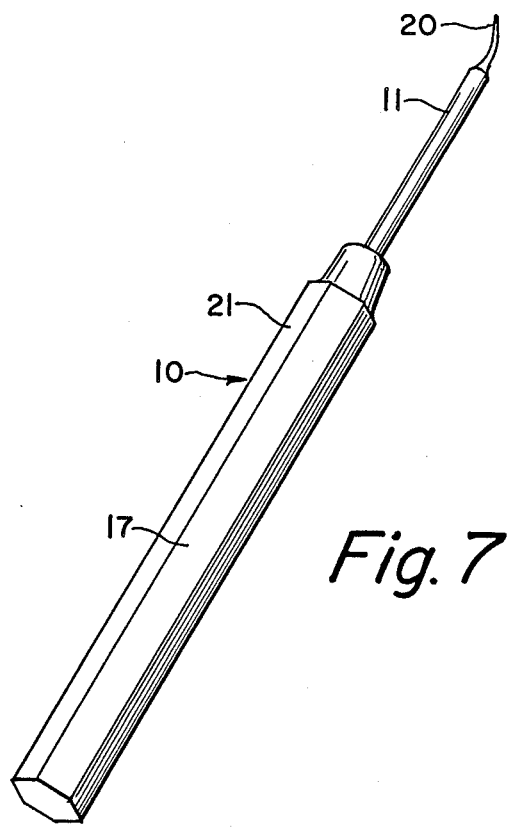
FIG. 7 is a perspective illustration of a preferred embodiment of the present microsurgery tool illustrating a handle to which the tool is fastened.

The microsurgery tool, in a preferred embodiment, has an arcuate distal end 20 as illustrated in FIG. 7. The tool is secured to a handle member 21 which resembles a pencil and is of such size and shape to permit handling by an operating surgeon. The side walls of the handle member 21 may be circular in cross-section, or preferably, may define an equilateral figure such as a hexagon, octagon.

The operation of the present microsurgery tool will be described in relation to FIGS. 1 through 5 inclusive.

In those drawings, a left vessel 30 is secured by a clamping member 31 in abutment with a right vessel 32 which is secured by a clamping member 33. The open ends 34, 35 of the vessels 30, 32 respectively are confined in abutment by means of the clamping members 31, 33. Typical clamping members are shown in U.S. Pat. No. 4,553,542.

A normal vein or artery has a diameter of 0.4 to 1.5 millimeters.

In order to initiate the anastomosis method, two sutures 36, 37 are provided in the vessels 30, 31 in accordance with normal prior art procedures, preferably by employing microsurgery forceps to dilate end vessel end opening 34, 35 respectively. These two sutures 36, 37 are spaced apart on the periphery of the open ends 34, 35 and retain the vessels 30, 32 to permit completion of the anastomosis. The microsurgery tool 11 is introduced between the open ends 34, 35 of the vessels 30, 32 and the tines 12, 13 are inserted into the right-hand vessel 32 beneath its open end 35. The upper surface of the microsurgery tool 11 engages the inner wall of the right-hand vessel 32. Penetration of the tines 12, 13 into the right-hand vessel is about 1.0 millimeters. The throat 14 of the tool 11 is maintained partly outside the cut end 35. Approximately 0.5 millimeter of the throat 14 is outside the right-hand vessel and is visible to the operator. An arcuate suture needle 40 with a trailing suture 41 is introduced to the site with its point penetrating the outer wall of the vessel 32 in the region of the throat 14. The scoop-like shape of the throat 14 receives the point of the arucate suture needle 40 directing the point out from the open end 35 of the vessel 32.

Figure 1:
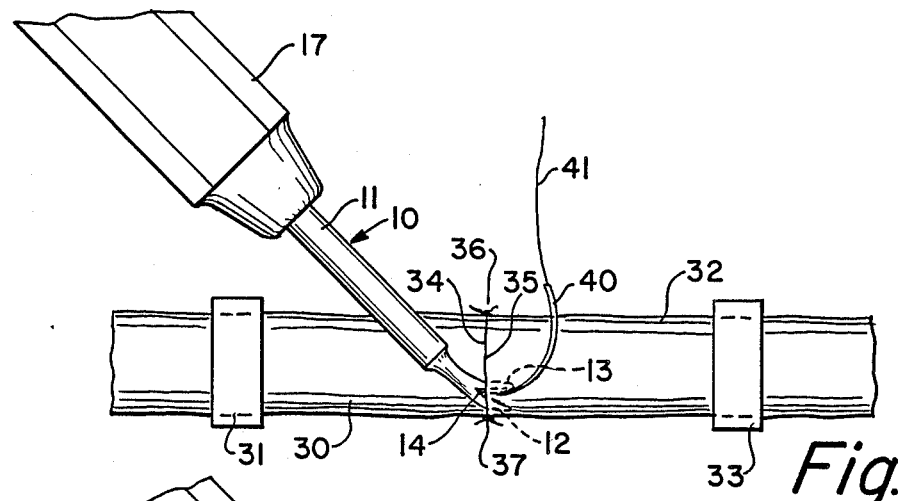
FIGS. 1, 2, 3, 4, 5 illustrate two vessel ends secured by clamping devices in abutment, illustrating the use of the tool of this invention in practicing the method of this invention.
Figure 2:
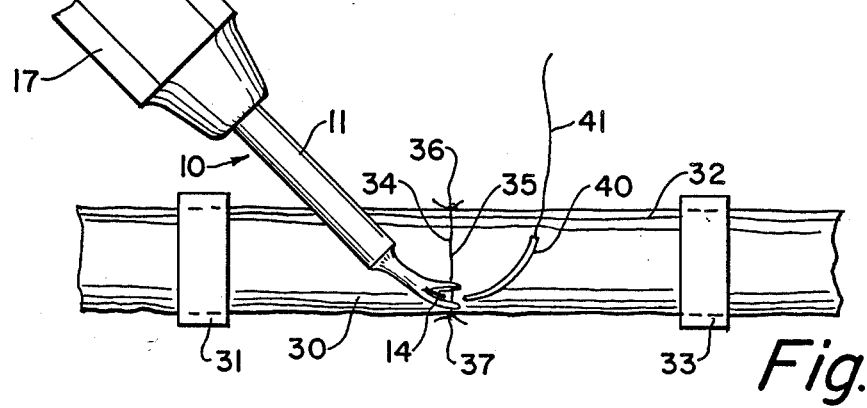
Figure 3:
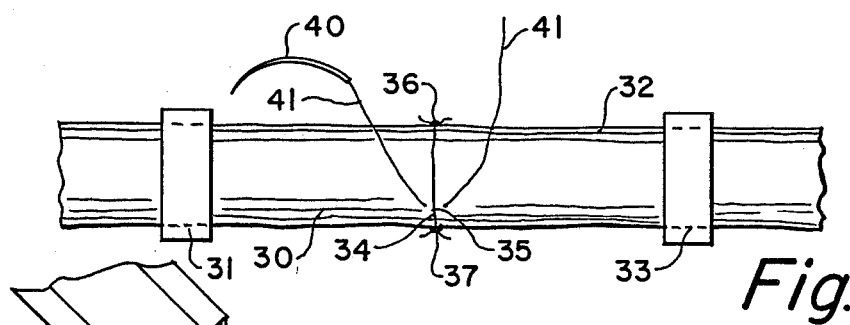
Figure 4:
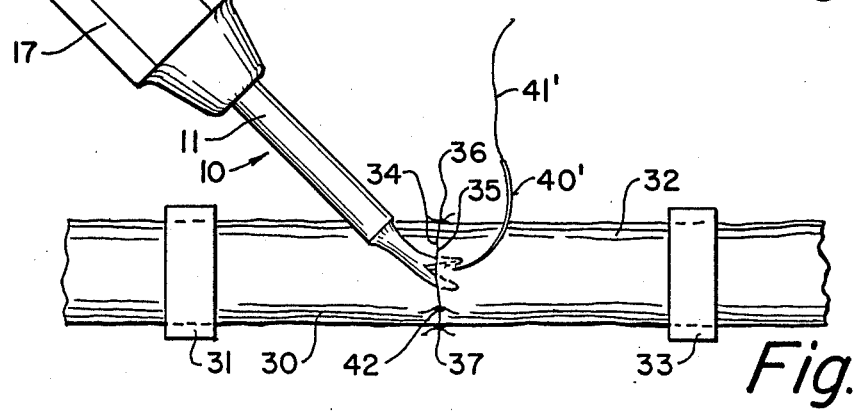

The microsurgery tool 11 is then withdrawn from the opening between the open ends 34, 35 and is positioned as shown in FIG. 2 with its bottom surface engaged with the outer wall of the left hand vessel 30. The arcuate suture needle 40 punctures the inner wall of the vessel 30 beneath the throat 14 and penetrates the vessel wall upwardly, guided by the scoop-like shape of the throat 14. Thereafter the microsurgery tool 11 is withdrawn from the site and the arcuate suture needle 40 is extracted through the suture openings in the vessels 30, 32 with the trailing suture 41 being drawn into a position where the suture ends (FIG. 3) can be tied to form a suture 42 as shown in FIG. 4. Thereafter the microsurgery tool 11 is introduced into the opening between the open ends 34, 35 and contacts the inner wall of the right-hand vessel 32. The microsurgery tool 11 is used in combination with an arcuate suture needle 40' which is secured to a trailing suture 41' and the process described in FIGS. 1, 2, 3 is repeated to produce an additional suture 43 as shown in FIG. 5.

Figure 5:
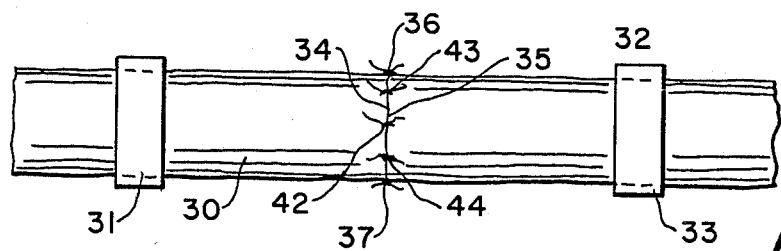

When the anastomosis is complete, uniform sutures (36, 37, 42, 43, 44, are shown in FIG. 5) along with other sutures (not seen in FIG. 5) will present the number of sutures required to complete the anastomosis.

The preferred embodiment of the microsurgery tool 10 includes an arcuate distal end 20 (FIG. 7). The microsurgery tool 10 can be formed with a straight shaft 11 as shown in FIG. 6.

The thin shaft 11 preferably is formed from surgical steel although appropriate inert plastic substances can be employed for convenience and to reduce expenses. It may be preferred to provide a set of the microsurgery tools of differing dimensions as might be required to complete a particular anastomosis procedure. The set might include individual tools or interchangeable shafts 11 for standard suture needles. Typical needles in blood vessel anastomosis procedures are No. 10 (100 microns thickness) and No. 11 (75 microns thickness). The throat 14 of the microsurgery tool 10 should be large enough to receive the cooperating suture needles. The tools 10 can be recovered, sterilized and reused. The shafts 11 may be permanently secured in holding elements such as the handle 21 of FIG. 7 or the shafts may be detachably secured to a holding element by pressfit or positive mechanical connection.

In the improved method of this invention, anastomosis procedures are accelerated and are completed without excessive deformation of the vessels. Because of the close tolerances in the anastomosis procedure for small vessels, the microsurgery tool achieves a positive penetration of a suture needle in both vessels which are being connected.

The procedure is illustrated in the drawings for a butt-to-butt connection of two vessels. It should be understood that essentially the same procedure can be carried out with an end-to-side anastomosis of the type which is well known in the art and which is illustrated, for example, in the aforementioned U.S. Pat. No. 4,474,181.

The present microsurgery tool as well as the anastomosis procedure can employ the anastomosis ring described in U.S. Pat. Nos. 4,474,181 and 4,553,542.

We claim:

1. A microsurgery tool for use in combination with a microsurgery suture needle to anastomosize small vessels, comprising:
    a thin shaft secured at one end to a holding member and having, at its distal end a pair of projecting tines defining a sloping throat therebetween,
    said shaft being adapted to enter into a small vessel through a cut in said vessel and being further adapted to receive in said sloping throat the pointed end of a microsurgery suture needle penetrating said vessel adjacent to said cut.

2. The microsurgery tool of claim 1 in which the said sloping throat has a scoop-like shape to direct the path of a suture needle point advancing in the said throat.

* * * * *